US006195582B1

(12) United States Patent
Scott

(10) Patent No.: US 6,195,582 B1
(45) Date of Patent: Feb. 27, 2001

(54) ELECTROTRANSPORT DEVICE ELECTRODE ASSEMBLY HAVING LOWER INITIAL RESISTANCE

(75) Inventor: Erik R. Scott, Golden Valley, MN (US)

(73) Assignee: ALZA Corporation, Mountain View, CA (US)

( * ) Notice: Subject to any disclaimer, the term of this patent is extended or adjusted under 35 U.S.C. 154(b) by 0 days.

(21) Appl. No.: 09/239,708

(22) Filed: Jan. 28, 1999

Related U.S. Application Data

(60) Provisional application No. 60/072,806, filed on Jan. 28, 1998, provisional application No. 60/072,827, filed on Jan. 28, 1998, provisional application No. 60/072,823, filed on Jan. 28, 1998, provisional application No. 60/072,906, filed on Jan. 28, 1998, and provisional application No. 60/072,838, filed on Jan. 28, 1998.

(51) Int. Cl.[7] .......................................... A61N 1/30
(52) U.S. Cl. .................................. 604/20; 604/19
(58) Field of Search ...................... 604/20, 19; 617/149

(56) References Cited

U.S. PATENT DOCUMENTS

| | | | |
|---|---|---|---|
| 4,383,529 | 5/1983 | Webster | 604/20 |
| 4,744,787 | 5/1988 | Phipps et al. | 604/20 |
| 4,747,819 | 5/1988 | Phipps et al. | 604/20 |
| 5,047,007 | * 9/1991 | McNichols et al. | 604/20 |
| 5,084,008 | 1/1992 | Phipps | 604/20 |
| 5,147,297 | 9/1992 | Myers et al. | 604/20 |
| 5,246,417 | * 9/1993 | Haak et al. | 604/20 |
| 5,326,341 | * 7/1994 | Lew et al. | 604/20 |
| 5,356,632 | 10/1994 | Gross et al. | 424/449 |
| 5,362,307 | 11/1994 | Guy et al. | 604/20 |
| 5,387,189 | 2/1995 | Gyory et al. | 604/20 |
| 5,405,317 | 4/1995 | Myers et al. | 604/20 |
| 5,466,217 | 11/1995 | Myers et al. | 604/20 |
| 5,573,503 | 11/1996 | Untereker et al. | 604/20 |
| 5,622,530 | 4/1997 | Phipps | 604/20 |

FOREIGN PATENT DOCUMENTS

| | | | |
|---|---|---|---|
| WO 90/04432 | 5/1990 | (WO) | A61N/1/00 |
| WO 90/04433 | 5/1990 | (WO) | A61N/1/00 |
| WO 94/17853 | 8/1994 | (WO) | A61N/1/30 |
| WO 95/27530 | 10/1995 | (WO) | A61N/1/30 |
| WO 96/09851 | 4/1996 | (WO) | A61N/1/30 |
| WO 96/39224 | 12/1996 | (WO) | A61N/1/30 |

\* cited by examiner

*Primary Examiner*—Sharon Kennedy
*Assistant Examiner*—Jeremy Thissell
(74) *Attorney, Agent, or Firm*—Owen J. Bates; D. Byron Miller; Steven F. Stone

(57) ABSTRACT

The present invention relates generally to an electrotransport device for transdermally or transmucosally delivering a beneficial agent (e.g., a drug) to the body surface of a patient or for transdermally or transmucosally sampling a body analyte. Most particularly, the present invention relates to a configured and electrochemically reactive electrode assembly having improved start-up electrical performance and improved lag time to compliant agent delivery.

39 Claims, 5 Drawing Sheets

ELECTROTRANSPORT DEVICE ELECTRODE ASSEMBLY HAVING LOWER INITIAL RESISTANCE

This applications claims the benefits of provisional application nos.: U.S. Ser. No. 60/072,806, filed Jan. 28, 1998; U.S. Ser. No. 60/072,827, filed Jan. 28, 1998; U.S. Ser. No. 60/072,823, filed Jan. 28, 1998; U.S. Ser. No. 60/072,906, filed Jan. 28, 1998 and U.S. Ser. No. 60/072,838, Jan. 28, 1998 under 35 U.S.C. §119(e).

TECHNICAL FIELD

The present invention relates generally to an electrotransport device for transdermally or transmucosally delivering a beneficial agent (e.g., a drug) to, or for transdermally or transmucosally sampling a body analyte (e.g., glucose) from, a patient. Most particularly, the present invention relates to a configured electrode assembly having improved electrical performance such as lower electrical resistance at device start-up and shorter time required to reach the prescribed transdermal agent flux.

BACKGROUND ART

As used herein, "electrotransport" refers generally to the delivery of at least one agent or drug (charged, uncharged, or mixtures thereof) through a membrane (such as skin, mucous membrane, or nails) wherein the delivery is at least partially electrically induced or aided by the application of an electric potential. As used herein, the terms "drug" and "agent" are used interchangeably and are intended to include any therapeutically active substance that when delivered into a living organism produces a desired, usually beneficial, effect. For example, a beneficial therapeutic agent may be introduced into the systemic circulation of a patient by electrotransport delivery through the skin.

Electrotransport processes have been found to be useful in the transdermal administration of drugs including lidocaine, hydrocortisone, fluoride, penicillin, dexamethasone, and many other drugs. A common use of electrotransport is in diagnosing cystic fibrosis by delivering pilocarpine iontophoretically. The pilocarpine stimulates production of sweat. The sweat is then collected and analyzed for its chloride content to detect the presence of the disease. More recently, "reverse" electrotransport methods have been used to transdermally extract body analytes such as glucose in order to measure blood glucose levels. For a description of reverse iontophoresis devices and methods for analyte sampling, see Guy et al. U.S. Pat. No. 5,362,307, the disclosures of which are incorporated herein by reference.

Electrotransport devices generally employ two electrodes, each positioned in intimate contact with some portion of the patient's body (e.g., the skin). For drug delivery, an active or donor electrode delivers the therapeutic agent (e.g., a drug) into the body. The counter, or return, electrode closes an electrical circuit with the donor electrode through the patient's body. A source of electrical energy, such as a battery, supplies electric current to the body through the electrodes. For example, if the therapeutic agent to be delivered into the body is positively charged (i.e., cationic), the anode is the donor electrode and the cathode is the counter electrode completing the circuit. If the therapeutic agent to be delivered is negatively charged (i.e., anionic), the cathode is the donor electrode and the anode is the counter electrode. The rate of drug delivery is generally proportional to the applied electrotransport current. For that reason, commonly used electrotransport systems employ electric circuitry that control the electric current applied by such devices. For body analyte extraction, an active or sampling electrode extracts the body analyte from the body. The counter, or return, electrode closes the electrical circuit with the active electrode through the patient's body. If the body analyte to be extracted from the body is cationic, the cathode is the active electrode and the anode is the counter electrode completing the circuit. If the body analyte to be extracted is anionic, the anode is the active electrode and the cathode is the counter electrode. In the case of glucose extraction, glucose being an uncharged molecule, either or both of the anode and cathode can be the active electrode. Since glucose will be extracted into both electrodes at relatively the same rate by the phenomenon of electroosmosis.

A widely used electrotransport process, iontophoresis (also called electromigration), involves the electrically induced transport of charged ions. Another type of electrotransport, called electroosmosis, involves the transdermal flow of a liquid solvent, containing an (eg, uncharged or non-ionic) agent to be delivered or sampled, under the influence of the applied electric field. Still another type of electrotransport process, called electroporation, involves forming transiently existing pores in a biological membrane (e.g., the skin) by applying high voltage pulses thereto. In any given electrotransport system, more than one of these processes may occur simultaneously to some extent.

Most transdermal electrotransport devices have an anodic and a cathodic electrode assembly, each electrode assembly being comprised of an electrically conductive electrode in ion-transmitting relation with an ionically conductive liquid reservoir which in use is placed in contact with the patient's skin. Gel reservoirs such as those described in Webster U.S. Pat. No. 4,383,529 are the preferred form of reservoir since hydrated gels are easier to handle and manufacture than liquid-filled containers. Water is by far the preferred liquid solvent used in such reservoirs, in part because many drug salts are water soluble and in part because water has excellent biocompatability, making prolonged contact between the hydrogel reservoir and the skin acceptable from an irritation standpoint.

The electrodes used in transdermal electrotransport devices are generally of two types; those that are made from materials that are not electrochemically reactive and those that are made from materials that are electrochemically reactive. Electrochemically non-reactive electrodes, such as stainless steel, platinum, and carbon-based electrodes, tend to promote electrochemical oxidation or reduction of the liquid solvent at the electrode/reservoir interface. When the solvent is water, the oxidation reaction (at the anodic electrode interface) produces hydronium ions, while the reduction reaction (at the cathodic interface) produces hydroxyl ions. Thus, one serious disadvantage with the use of electrochemically non-reactive electrodes is that pH changes occur during device operation due to the water oxidation and reduction reactions which occur at the electrode/reservoir interfaces. Oxidation and reduction of water can largely be avoided by using electrochemically reactive electrodes, as discussed in Phipps et al. U.S. Pat. No. 4,747,819. Preferred electrochemically oxidizable materials for use in the anodic electrode include metals such as silver, copper and zinc. Of these, silver is most preferred, as it has better biocompatability compared to most other metals. Preferred electrochemically reducible materials for use in the cathodic electrode include metal halides. Of these, silver halides such as silver chloride are most preferred. While these electrode materials provide an elegant solution to the problem of pH drift in the electrotransport reservoirs, they have their own set of problems. For example, a silver anode is oxidized to produce silver ions (Ag→Ag$^+$+e$^-$). The silver cations are delivered from the anode via iontophoresis into the patient's skin, where they cause grey or black discoloration as soon as the skin is exposed to sunlight. Attempts have been made to limit the electromigration of electrochemically generated silver ions from the anodic electrode. See for example Phipps et al. U.S. Pat. No. 4,747,819 and Phipps et al. WO 96/39224 which disclose using a halide drug salt in the anodic reservoir to provide halide ions which react with the electrochemically-generated silver ions to produce substantially insoluble silver halides, thereby preventing silver ions from migrating into the skin. See also Phipps et al WO 95/27530 which discloses using a halide resin in the anodic reservoir to provide halide ions which react with the electrochemically-generated silver ions to produce substantially insoluble silver halides, thereby preventing silver ions from migrating into the skin. Unfortunately, both of these approaches to preventing silver ion migration into the skin have their own disadvantages. For the first approach described in Phipps et al. U.S. Pat. No. 4,747,819 and Phipps et al. WO 96/39224, sometimes very large or "excess" amounts of halide drug salt must be loaded into the anodic reservoir in order to provide enough halide ions to prevent silver migration, particularly over longer drug delivery periods. This is disadvantageous because of the high cost of many drugs, thereby making this a costly solution to the silver migration problem. For the second approach described in Phipps et al WO 95/27530, the halide resins have been found to contain many impurities and unreacted monomeric components which cannot effectively be removed from the resins. At least some of these components have been found to cause undesireable skin irritation when the resins are used in electrotransport reservoirs, perhaps because the impurities are being transdermally delivered into the skin by the applied electrotransport current.

One potential solution to the metal ion migration problem encountered with oxidizable metal anodes is the use of intercalation compounds as taught in Phipps, et al, U.S. Pat. Nos. 4,747,819 and 5,573,503. While the use of intercalation compounds does avoid the problem of migration of metal ions into the patient's skin, at least some of these materials (e.g., polyanilines) have not been extensively used, in part because of their very high initial (i.e., at the time the electrotransport device begins applying electrotransport current) electrical resistance. The problem of high electrical resistance is discussed in more detail below in connection with prior art silver halide cathodes.

Hence, there is a need for an improved anodic electrode which does not have the problems of (1) competing metal ion generation as is found in anodes formed of conventional oxidizable metals, and/or (2) high initial electrical resistance.

On the cathode side, the silver halide cathodes produce only halide (eg, chloride) ions when they are electrochemically reduced (AgX→Ag+X$^-$). Although the electrochemically generated halide (e.g., chloride) ions do tend to be delivered from the cathode into the patient, chloride is naturally present in the body in fairly high amounts so delivery of chloride ions from the cathode has no adverse effects. Thus, while the silver halide cathodes are quite biocompatible, they have one serious disadvantage in that they are substantially non-conductive, at least until enough of the silver halide has been reduced to form metallic silver. This is similar to the problem of high initial electrical resistance found in anodes formed of intercalation compounds such as polyanilines, which anodes don't conduct significant amounts of electric current until enough of the, eg, polyaniline has been oxidized. This may cause a delay in the start of compliant device operation because the silver halide cathode and/or the polyaniline anode has too high an electrical resistance for the relatively small voltages supplied by the small (eg, coin cell) batteries which are used to power small patient-worn electrotransport devices. Of course, electrochemical reduction of the silver halide to form metallic silver, and the electrochemical oxidation of the reduced (i.e., leuco) form of polyaniline to form a more conductive (i.e., an oxidized or emaraldine) form of polyaniline gradually takes place at the interface between the electrode and the liquid electrolyte in accordance with the following reactions:

Anodic polyaniline (PA) oxidation: 
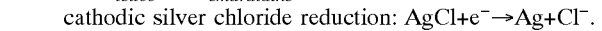

cathodic silver chloride reduction: AgCl+e$^-$→Ag+Cl$^-$.

The reduction of the leuco form of polyaniline is discussed in detail in Cushman et al., "Spectroelectrochemical Study of Polyaniline: the Construction of a pH-potential phase diagram", Journal of Electroanalytical Chemistry, 291 (1986), 335–346. Although the formation of metallic silver at the cathode/liquid electrolyte interface and the formation of oxidized polyaniline at the anode/liquid electrolyte interface gradually improves the electrical conductivity of the electrode, it is a fairly slow process. As a result, traditional electrode configurations like that shown in FIG. 1 are undesirable because of their high electrical resistance at the beginning of electrotransport device operation. The electrode assembly 50 shown in FIG. 1 includes a housing 20 with a depression or well 25 which contains an electrode 52, an electrolyte reservoir 53 and a conductive current collector 51. Current collector 51 comprises a portion of the electrical connection between the electrode 52 and the device power source (not shown in FIG. 1), the other portions of the electrical connection include a metal contact (ie, a tab) 58 and a conductive member 72 which could be a metal wire but more typically is formed by depositing a conductive trace on a non-conductive circuit board 18. Initially, electrode 52 has a high electrical resistance, and therefore acts to insulate the conductive current collector 51 from the electrolyte reservoir 53, which is typically a gel. Due to such insulation, insufficient flow of electrons are available to or from the interface 56 between the electrolyte reservoir 53 and the electrode 52, severely inhibiting the oxidation or reduction of the redox material, thus, causing a higher electrical resistance across the electrode 52. That is, there is a large initial voltage drop across the electrode 52.

The electrical resistance of the electrode 52 is calculated from Ohm's Law: $R_{electrode}=\Delta V/i$, wherein $\Delta V$ is the voltage drop across the electrode and i is the applied current. The electrical resistance at one "side" (ie, either the anodic side or the cathodic side) of an electrotransport device is generally considered to be the sum of the resistances of (1) the electrode assembly, and (2) the patient body surface to which the electrode assembly is applied (e.g., the skin). Although the initial skin resistance is generally quite high (e.g., more than about 50,000 ohm-cm)$^2$ when an electrotransport device is first turned on, the skin resistance drops very quickly during the first 2 to 5 minutes of device operation to a level which is well within the compliant range of electrotransport device power sources, which typically apply voltages in the range of 2 to 10 volts. During this period, because it is important that all available energy is used for overcoming the skin's resistance, any excess voltage drop due to a resistive electrode will diminish the current available for therapy. If the electrode resistance is above a predetermined amount, compliance is lacking, which means that the device is unable to apply the prescribed current because the electrode resistance is too great for the limited voltage of the power source. Unfortunately, the electrical resistance of polyaniline anodes and silver halide cathodes does not drop quickly like human skin. Thus, there can be a long wait (e.g., more than 30 minutes) until the electrode resistance drops to a level at which the electrotransport device becomes compliant and can deliver the prescribed electrical current. This delay in reaching device compliance is also referred to as the start-up lag-time). During this start-up lag-time, the anode resistance drops as the, eg, polyaniline, reacts to form electrically conductive oxidized polyaniline, and the cathode resistance drops as the silver halide reacts to form electrically conductive metallic silver. More importantly, the lag time to compliant drug delivery makes the use of polyaniline anodes and silver halide cathodes in electrotransport drug delivery unacceptable for many applications. For example, many applications for transdermal electrotransport drug delivery require a very short lag time to compliance, such as delivery of an antimigraine drug to treat migraines or delivery of a narcotic analgesic to treat pain.

Of course, the delay in reaching compliant electrotransport device operation can be reduced by increasing the battery voltage, but this requires more (or more expensive) batteries to power the device which undesirably increases the cost of electrotransport drug delivery. The delay in reaching compliant electrotransport device operation can also be overcome by adding electrically conductive fillers, such as powdered metal or carbon, to the intercalation anode or to the silver halide cathode as taught in Myers et al. U.S. Pat. No. 5,147,297. However, this makes the manufacture of these electrodes more difficult since the conductive fillers must have very good and even distribution throughout the electrode matrix and also makes the electrodes more expensive.

Hence, there is a need for an improved electrode for an electrotransport device that achieves compliant agent delivery quickly, without significant voltage drop due to high initial electrical resistance, and without the need for significant power supply voltages or other expensive conductive fillers to overcome any significant initial electrode resistance.

DESCRIPTION OF THE INVENTION

The present invention overcomes the disadvantages associated with the prior art electrode assembly 50 shown in FIG. 1, whereby the electrode 52 initially acts as a high electrical resistance barrier between the current collector 51 and the interface 56 between the electrolyte reservoir and the redox species contained in electrode 52. The present invention provides an electrotransport device for delivering or sampling an agent through a body surface, such as skin. The device includes a pair of electrode assemblies, one anodic and one cathodic, both electrically connected to a source of electrical power (e.g., one or more batteries). At least one of the electrode assemblies includes an electrode, a current collector connecting the electrode to the power source, and an electrolyte reservoir in ion-transmitting relation to the electrode. In use, the electrolyte reservoir is positioned in ion-transmitting relation with the body surface (e.g., skin).

The electrode is composed at least in part of a solid phase electrochemically reactive (i.e., electrochemically oxidizable or reducible) material. The electrode has a high initial electrical sheet resistance, typically greater than about 100 ohm/square which is lessened by exposure of the electrode to electric current. Upon such exposure, the electrochemically reactive material is oxidized or reduced to a form having a lower electrical resistance, such that the sheet resistance of the electrode is lowered below its initial sheet resistance.

The current collector has a low initial resistance (ie, it is highly conductive) and comprises at least part of the electrical connection between the device power source and the electrode. Thus, the current collector conducts electric current between the power source and the electrode.

At the time when the electrotransport device begins applying electrotransport current, the electrode, the current collector and the electrolyte reservoir form a common boundary. The common boundary condition gives the electrode assemblies of the present invention a shorter lag-time for achieving compliant electrotransport delivery and lower initial electrical resistance, thereby requiring lower power source voltages for device operation.

The electrode assembly of the present invention can be either (1) an anodic electrode assembly wherein the electrode is composed of a resistive oxidizable material such as the leuco form of polyaniline, or (2) a cathodic electrode assembly wherein the electrode is composed of a resistive reducible material such as a silver halide.

MODES FOR CARRYING OUT THE INVENTION

Definitions

Figure 1:
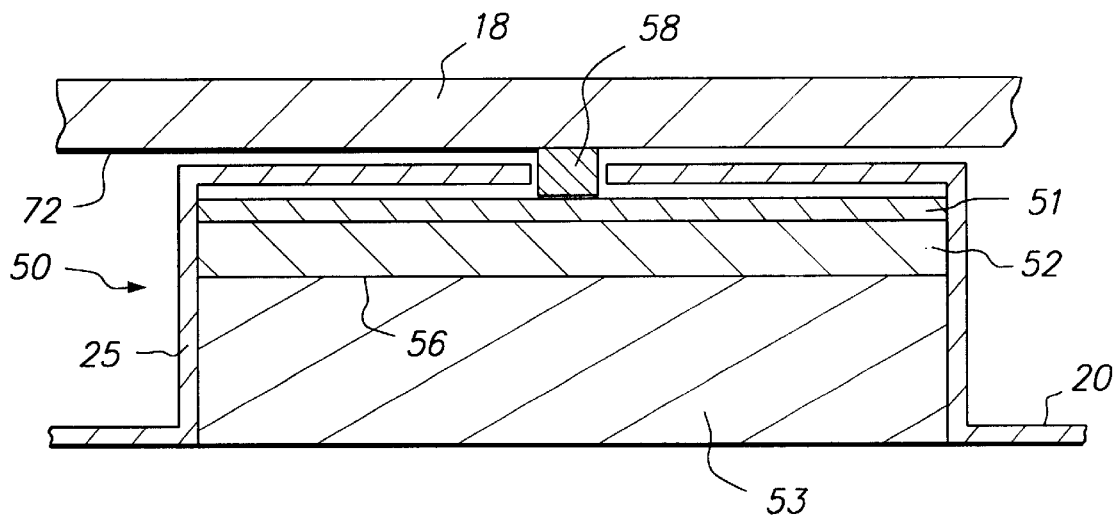
FIG. 1 is a cross sectional view of a prior art configuration of an electrotransport electrode assembly.

As used herein, the term "electrochemically reactive material" means a compound or composition capable of being electrochemically oxidized or reduced and wherein the reacted (i.e., oxidized or reduced) form of the material has a lower electrical resistance than the unreacted form (i.e., oxidizable or reducible form, respectively) of the material. This term also includes intercalation host materials, which may themselves be directly oxidized or reduced, or may intercalate dopants that become oxidized or reduced.

As used herein, the term "common boundary" means a macroscopic and measurable intersection of the current collector, the electrode, and the electrolyte reservoir.

As used herein, the term "electrode assembly" includes a collection of at least the following three elements: a current collector, an electrode and an electrolyte reservoir.

As used herein, the term "electrical sheet resistance" is the surface resistance between opposite edges of a unit square of a material. Electrical sheet resistance (also sometimes called surface resistivity in the literature) is generally designated in the literature by the symbol $\rho_S$ and is used to characterize current flow over a surface. The resistance across a square is independent of the size of the square and the unit of sheet resistance is the ohm, or more superfluously (and as used herein), ohm/square. Since a conducting surface is always a layer with a finite thickness, t, the sheet resistance is related to the volume resistivity, $\rho_{P\,V}$, of the layer by the following equation: $\rho_S = \rho_V \div t$. The sheet resistance of any given electrode or current conductor can be measured in accordance with the methods described in The American Society for Testing and Materials (ASTM), West Conshohocken, Pa., volume 10.02, Test Standard Designation D 4496-87 (reapproved 1993), entitled "Standard Test Method for D-C Resistance or Conductance of Moderately Conductive Materials", the disclosures of which are incorporated herein by reference.

As used herein, the term "body surface" includes the skin, mucosal membranes and/or nails of a living animal. In particular, it includes the skin of living humans.

As used herein, the term "electrolyte reservoir" means a liquid which contains, or which receives during device operation, dissolved ions. The term includes saline solutions used in counter electrodes and drug solutions or suspensions in donor electrodes. The term also includes matrices such as a sponge, fabric, or a polymer such as a gel which contains such a solution or suspension. The term includes both aqueous solutions and non-aqueous solutions (e.g., solutions of dissolved electrolyte in a glycol or glycerol).

As used herein, the term "compliant agent delivery" means that the agent is being delivered via electrotransport through the body surface at the prescribed electrotransport current. There is not compliant agent delivery when an electrotransport device is unable to supply the prescribed electrotransport current, even at the maximum applied voltage, because the device components and/or the skin have too high an electrical resistance.

As used herein, the term "lag time" means the period of time during which an electrotransport device applies a non-compliant current. In general, the lag time is measured from the time when the electrotransport device begins applying electrotransport current until the time when the prescribed electrotransport current begins to be applied.

Figure 2:
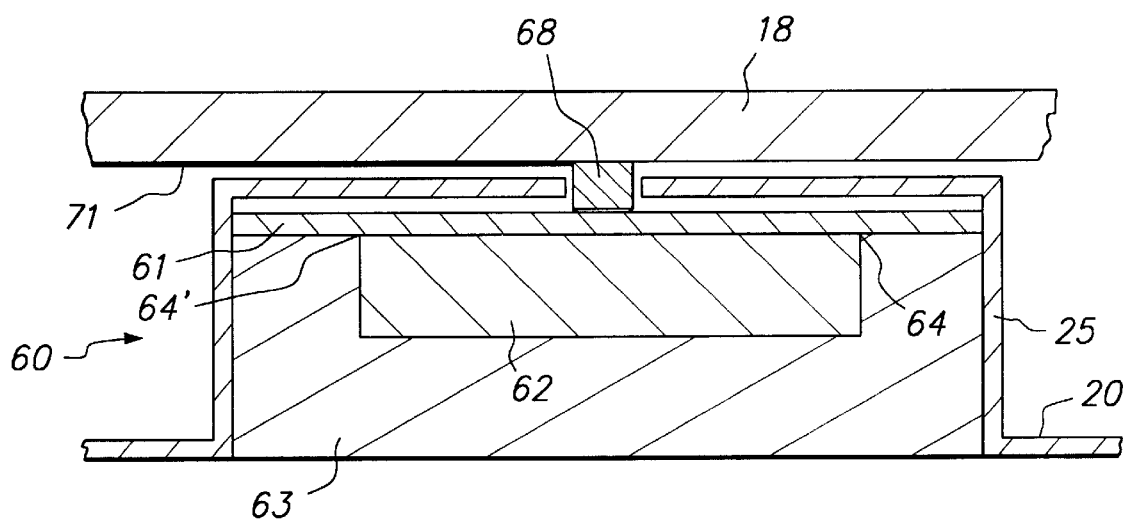
FIG. 2 is a cross sectional view of an exemplary configuration of an electrotransport electrode assembly of the present invention.

FIG. 2 illustrates one example of an electrode assembly 60 in accordance with the present invention. Similar to the prior art electrode assembly 50, electrode assembly 60 also includes a housing 20 having a well or depression 25 which contains a current collector 61, an electrode 62 and an electrolyte reservoir 63. The current collector 61 comprises a portion of the electrical connection between the electrode 62 and the device power source (not shown in FIG. 2), the other portions of the electrical connection including a metal contact (i.e., a tab) 68 and a conductive circuit 71, typically formed of a conductive trace deposited on a non-conductive circuit board 18. Like the electrode assembly 50 shown in FIG. 1, the electrode assembly 60 of the present invention includes an electrode 62 composed of a redox material which initially has a high electrical resistance. In general, the electrode 62 has an initial electrical sheet resistance of greater than about 100 ohm/square and preferably greater than about 10,000 ohm/square the electrode 62 being oxidizable or reducible to a form having a lower electrical sheet resistance than its initial electrical sheet resistance. The redox material of electrode 62 should be solid phase and should not readily dissolve in the liquid phase of the adjacent electrolyte reservoir 63. Preferably, the redox material has a solubility in the liquid within electrolyte reservoir 63 of less than about 1 mg/ml. Most preferably, the electrode 62 is completely, or substantially completely, composed of the redox material.

Unlike the electrode assembly 50 of the prior art, the electrode assembly 60 of the present invention utilizes an electrode 62 which has smaller lateral dimensions (i.e., length and/or width) than the current collector 61, resulting in a common boundary 64, 64' between the current collector 61, the electrode 62 and the electrolyte reservoir 63. The common boundary 64, 64' provides a region in which the electrons carried by current collector 61, the redox material contained within electrode 62 and the electrolyte reservoir 63 are all in immediate contact with one another. The provision of these three elements in close proximity greatly reduces the initial electrical resistance of the electrode assembly 60 compared to the initial electrical resistance of electrode assembly 50 which provides no such common boundary condition.

In the case where electrode assembly 60 is a cathodic electrode assembly, the electrode 62 is a cathode comprised of an electrochemically reducible material such as silver chloride. Silver chloride is a solid phase redox material which is substantially water insoluble. Thus, when the liquid within reservoir 63 is an aqueous liquid, the silver chloride does not appreciably dissolve in the liquid in reservoir 63. The electrolyte reservoir 63 is typically in the form of a polymeric gel containing a liquid electrolyte. In the case where the electrode assembly 60 is a donor electrode assembly, the liquid electrolyte within the gel is typically a drug solution. In the case where the electrode assembly 60 is a counter electrode assembly, the liquid electrolyte within the gel is typically saline.

Figure 3:
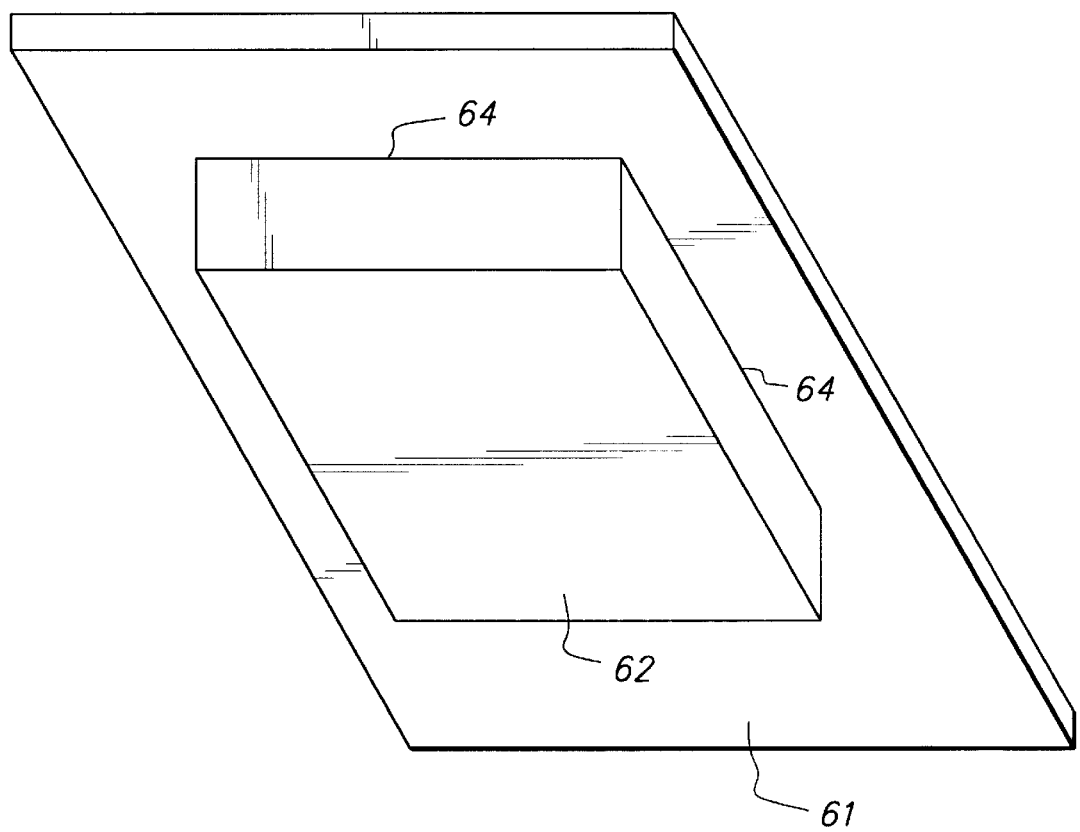
FIG. 3 is a bottom perspective view of an electric current collector and an electrode of the present invention.

A perspective view of the current collector 61 and the electrode 62 is shown in FIG. 3. The electrolyte reservoir 63 is removed to better show the common boundary 64. In this embodiment, the common boundary 64 comprises four lines, which together form the shape of a rectangle.

Preferably, the current collector 61 has a sheet resistance that is less than one-half the sheet resistance of the electrode 62. More preferably, the current collector 61 has a sheet resistance less than about 50,000 ohm/square, even more preferably less than about 1000 ohm/square, and most preferably less than about 10 ohm/square. The current collector 61 can be a metallic or carbon foil (e.g., silver, stainless steel, platinum or graphite) or can be a polymeric film loaded with a conductive filler such as carbon fibers, carbon particles or metal particles. Most preferably, the current collector 61 is in the form of an electrically conductive trace or an electrically conductive adhesive comprised of an adhesive polymeric binder containing metal and/or carbon conductive fillers. The adhesive adheres to both the contact 68 and the electrode 62 in order to maintain good electrical continuity between these elements.

As the reduction reaction proceeds at the surface of cathodic silver chloride electrode 62, the reduction of silver chloride initially occurs at the common boundary 64,64' producing metallic silver causing the region proximate to the common boundary 64,64' to become more electrically conductive. As the device operates, the reduction of silver chloride proceeds, eventually covering the entire outer surface of cathodic electrode 62.

At the common boundaries 64,64', the electrode 62 is quickly reduced because the current collector 61 provides a ready supply of electrons and because the liquid in the electrolyte reservoir 63 is available for the ions to migrate setting up an electrotransport current comprised of ions flowing between the electrolyte reservoir 63 and the patient's body surface. For example, when the electrode 62 includes silver chloride, the silver chloride is reduced, producing Ag metal and chloride ions. Anions within the electrolyte reservoir 63 migrate to the body surface establishing a current for delivering or sampling an agent. Agent is delivered or sampled through the skin at a compliant delivery rate without any significant voltage drop or lag time at the cathode because silver chloride is quickly and abundantly reduced all along the common boundaries 64,64'.

In contrast, as shown in FIG. 1, the prior art electrode assembly 50 has an electrode 52 which shares no common boundary with the current collector 51 and the electrolyte reservoir 53. The interface 56 between the silver chloride electrode 52 and the electrolyte reservoir 53 has no ready supply of electrons because the silver chloride electrode 52 is substantially non-conductive. Thus, the electrode 52 substantially insulates the electrons provided by the current collector 51 from reaching the boundary 56 between the electrolyte reservoir 53 and the electrode 52, thus, impeding reduction of the silver chloride at the interface 56 of electrode 52. Thus, the net effect of the increase in electrical resistance is that the compliance voltage of the circuit may be insufficient to initially achieve compliant agent delivery.

In the case where electrode assembly 60 is an anodic electrode assembly, the electrode 62 is an anode comprised of an electrochemically oxidizable material such as polyaniline. The electrolyte reservoir 63 is typically in the form of a polymeric gel containing a liquid electrolyte. In the case where the electrode assembly 60 is a donor electrode assembly, the liquid electrolyte within the gel is typically a drug solution. In the case where the electrode assembly 60 is a counter electrode assembly, the liquid electrolyte within the gel is typically saline.

As the oxidation reaction proceeds at the surface of anodic polyaniline (leuco form) electrode 62, the oxidation of polyaniline initially occurs at the common boundary 64,64' producing oxidized polyaniline (emaraldine form, which is more electrically conductive than the reduced leuco form of polyaniline) causing the region proximate to the common boundary 64,64' to become more electrically conductive. As the device operates, the oxidation of polyaniline proceeds, eventually covering the entire outer surface of anodic electrode 62.

At the common boundaries 64,64', the electrode 62 is quickly oxidized because the current collector 61 provides a ready of electrons and because the liquid in the electrolyte reservoir 63 is available for the ions to migrate setting up an electrotransport current comprised of ions flowing between the electrolyte reservoir 63 and the patient's body surface. For example, when the electrode 62 includes leuco-polyaniline, the leuco-polyaniline is oxidized, producing electrically conductive oxidized polyaniline. Cations within the electrolyte reservoir 63 migrate to the body surface establishing a current for delivering or sampling an agent. Agent is delivered or sampled through the skin at a compliant delivery rate without any significant voltage drop or lag time at the anode because polyaniline is quickly and abundantly oxidized all along the common boundaries 64,64'.

In contrast, as shown in FIG. 1, the prior art electrode assembly 50 has an electrode 52 which shares no common boundary with the current collector 51 and the electrolyte reservoir 53. The interface 56 between the e.g., leuco-polyaniline electrode 52 and the electrolyte reservoir 53 has no ready drain of electrons because the polyaniline electrode 52 is initially (i.e., before significant oxidation has taken place) substantially non-conductive. Thus, the electrode 52 substantially insulates the current collector 51 from the boundary 56 between the electrolyte reservoir 53 and the electrode 52, thus, impeding oxidation of the leuco-polyaniline at the interface 56 of electrode 52. Thus, the net effect of the increase in electrical resistance is that the compliance voltage of the circuit may be insufficient to deliver the desired or necessary therapeutic current.

The common boundary between the current collector 61, the electrode 62 and the electrolyte reservoir 63 can have any shape or configuration as long as at least one common boundary exists and as long as the common boundary has sufficient length to reduce the unacceptably high initial electrical resistance of electrode 62 to an overall acceptable initial resistance for the electrode assembly 60. For example, the electrode 62 may be offset from the current collector 61, forming a single common boundary (64 or 64'). Alternatively, the common boundary may be circular, triangular, elliptical, or any other shape (individually or collectively) so long as there is at least one common boundary. Alternatively, the electrode 62 may have a hole or slot of any shape (eg, a donut-shaped electrode) allowing the electrolyte reservoir 63 to directly contact the current collector 61.

In some instances, it may be desirable to coat the electrode 62 and/or the current collector 61 with a thin layer of a material such as an adhesive or a hydrophilic surface coating in order to improve the adhesion or hydrophilicity of the electrode 62 and/or the current collector 61, either to improve the adhesion between the electrode 62 and the current collector 61 or to improve the adhesion of these elements to the electrolyte reservoir 63. A hydrophilic surface coating on the electrode 62 and/or the current collector 61 may also be used to improve the surface interaction between either or both of these elements and the (e.g., aqueous) electrolyte reservoir 63. Such coatings may act to physically separate the electrode 62 and/or the current collector 61 from the electrolyte reservoir 63. However, as long as any such coatings on electrode 62 and/or current collector 61 are thin and either electrically or ionically conductive, then the coatings should not be considered an impediment to a common boundary which would otherwise be present, but for the coating(s).

The minimum necessary length of the common boundary will be dependent upon a number of factors including the maximum voltage which can be applied by the power source, the prescribed level of electrotransport current as well as the initial sheet resistance of the electrode 62. In general, small electrotransport transdermal delivery and sampling devices adapted to be worn unobtrusively under clothing will have power sources with maximum voltages in the range of less than about 20 volts, and more typically in the range of about 2 to 10 volts. Furthermore, such devices typically apply electrotransport currents of less than 1 mA, and more typically less than 0.5 mA. Furthermore, electrodes formed of a polymeric component containing a redox species in particle form (e.g., a polyisobutylene matrix containing silver chloride particles) will typically have an electrical sheet resistance of greater than about 1,000 ohm/square and more typically greater than about 10,000 ohm/square. Under such "typical conditions", the common boundary length should be at least about 0.1 cm and preferably at least about 1 cm. Expressed in terms of the ratio of common boundary length (I) to applied electrotransport current (i), the ratio should be at least 0.1 cm/mA and preferably at least about 1 cm/mA.

Figure 5:
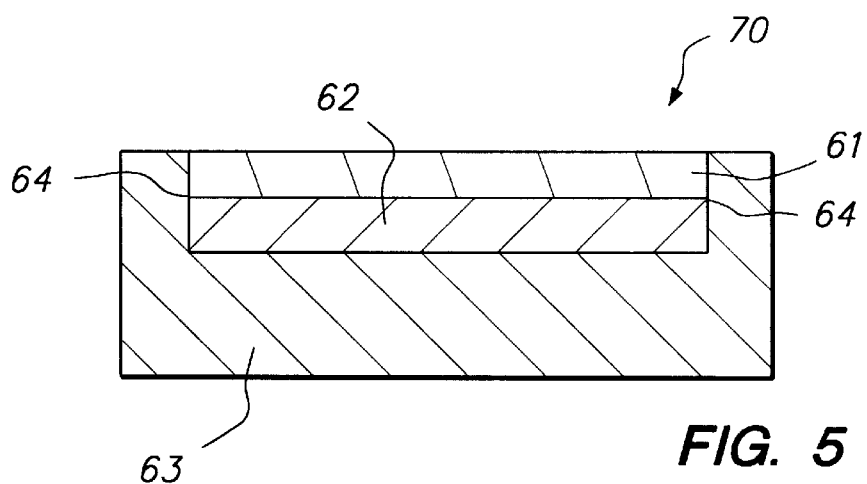
FIG. 5 is a cross sectional view of an electrode assembly of the present invention.

Shown in FIG. 5 is another example of an electrode assembly 70 of the present invention. In this configuration, the facing sides of electrode 62 and the current collector 61 have the same surface area and are laminated together to form a bi-layer laminate structure. As a result, the common boundary 64 is on the edge of the electrode 62/current collector 61 laminate.

Figure 6:
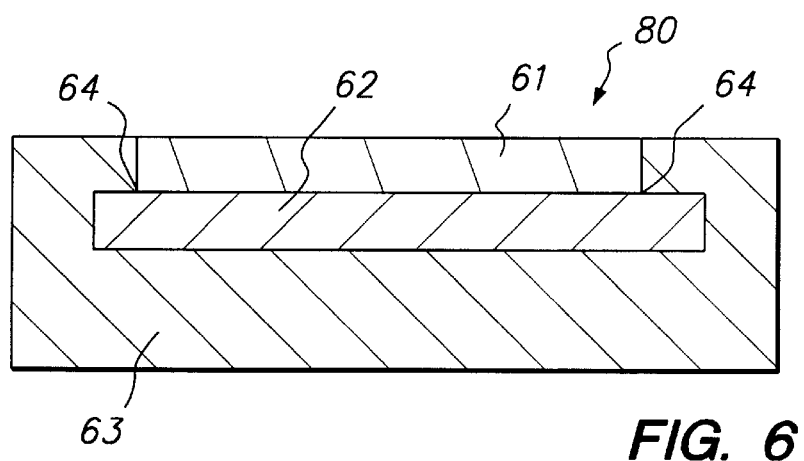
FIG. 6 is cross sectional view of another electrode assembly of the present invention.

Shown in FIG. 6 is another example of an electrode assembly 80 of the present invention. In this configuration, the electrode 62 is wider than the current collector 61. As a result, the common boundary 64 is beneath the "overhang" of the electrode 62.

Figure 7:
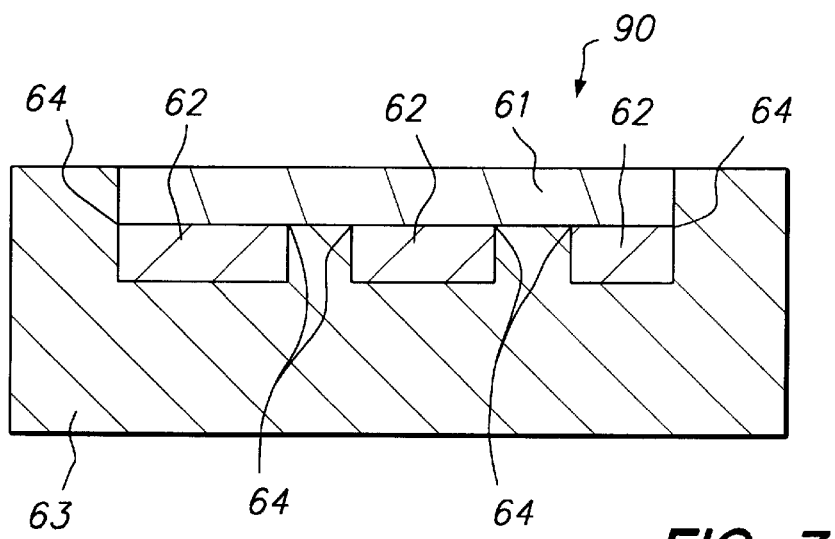
FIG. 7 is a cross sectional view of still another electrode assembly of the present invention; and, FIG. 8 is a graph of cathode voltage versus time, illustrating the reduced lag time, during electrotransport device start-up, of a cathodic electrode assembly of the present invention.

Shown in FIG. 7 is another example of an electrode assembly 90 of the present invention. In this configuration, a plurality of electrodes 62 are laminated to the current collector 61 with spaces therebetween. The electrolyte reservoir 63 contacts the current collector 61 to form a plurality of common boundaries 64. Other configurations are contemplated by the present invention so long as a common boundary of sufficient length is present. The configurations shown in FIGS. 2 through 7 are merely illustrative.

In general, the electrode 62 comprises a material which is initially in a highly resistive state, but which when oxidized or reduced becomes less resistive. In the case of a cathodic electrode 62, the electrode is composed, at least in part, of an electrochemically reducible material. The reducible material can be selected from metal compounds, metal complexes, intercalation compounds, carbon intercalation hosts hosting an alkali metal, and electrochemically oxidizable or reducible polymers. A particularly preferred class of reducible materials are compounds defined by the formula MX, wherein M is a metal capable of being electrically reduced (other than alkaline earth metals) and X is selected from polymeric anions and low molecular weight anions such as halides, sulfates, and phosphates, but preferably a halide. Most preferably, X is chloride. Preferably, M is silver, zinc or copper, and more preferably silver. The most preferred electrochemically reducible material for use in cathodes of the present invention is substantially pure silver chloride.

Another type of reducible material for use in cathodes of the present invention is an intercalation compound such as an alkali metal tungstate. The reduction reaction shown for an alkali metal tungstate is as follows:

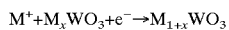

$$M^+ + M_xWO_3 + e^- \rightarrow M_{1+x}WO_3$$

wherein M is an alkali metal, preferably sodium.

Other reducible and oxidizable species are listed in the CRC Handbook of Chemistry and Physics, 57$^{th}$ Edition, D-141 to D-146, which is incorporated herein by reference.

The preferred electrochemically oxidizable material for use in anodes of the present invention is the leuco form of polyaniline.

As used herein, the term "agent" includes both agents which are sampled from the body, e.g., for diagnostic purposes, as well as, therapeutic agents which are delivered from the device into the body in order to achieve a therapeutic effect. In the context of sampling agents for diagnostic purposes, the agent can be any body analyte including electrolytes or glucose which are sampled in order to perform a diagnostic test such as measurement of blood glucose. In the context of therapeutic agent delivery, the term "agent" is used interchangeably with "drug", and each are intended to be given its broadest reasonable interpretation in the art as any therapeutically active substance which when delivered to a living organism produces a desired, usually beneficial, effect. For example, "agent" includes therapeutic compounds and molecules from all therapeutic categories including, but not limited to, anti-infectives (such as antibiotics and antivirals), analgesics (such as fentanyl, sufentanil, buprenorphine, and analgesic combinations), anesthetics, antiarthritics, antiasthmatics (such as terbutaline), anticonvulsants, antidepressants, antidiabetics, antidiarrheals, antihistamines, anti-inflammatories, antimigranes, antimotion sickness preparations (such as scopolamine and ondansetron), antineoplastics, antiparkinsonisms, antipruritics, antipsychotics, antipyretics, antispasmodics (including gastrointestinal and urinary), anticholinergics, sympathomimetrics, xanthine and derivatives thereof, cardiovascular preparations (including calcium channel blockers such as nifedipine, beta-agonists (such as dobutamine and ritodrine), beta blockers, antiarrythmics, antihypertensives (such as atenolol), ACE inhibitors (such as lisinopril), diuretics, vasodilators (including general, coronary, peripheral and cerebral), central nervous system stimulants, cough and cold preparations, decongestants, diagnostics, hormones (such as parathyroid hormones), hypnotics, immunosuppressives, muscle relaxants, parasympatholytics, parasympathomimetrics, prostaglandins, proteins, peptides, psychostimulants, sedatives and tranquilizers.

The electrotransport device of the present invention may also deliver drugs and/or agents including baclofen, beclomethasone, betamethasone, buspirone, cromolyn sodium, diltiazem, doxazosin, droperidol, encainide, fentanyl, hydrocortisone, indomethacin, ketoprofen, lidocaine, methotrexate, metoclopramide, miconazole, midazolam, nicardipine, piroxicam, prazosin, scopolamine, sufentanil, terbutaline, testosterone, tetracaine and verapamil.

The electrotransport device of the present invention may also deliver peptides, polypeptides, proteins, oligonucleotides, polysaccharides and other macromolecules. Such molecules are known in the art to be difficult to deliver transdermally or transmucosally due to their size. For example, such molecules may have molecular weights in the range of 300–40,000 daltons and include, but not limited to, LHRH and analogs thereof (such as buserelin, gosserelin, gonadorelin, naphrelin and leuprolide), GHRH, GHRF, insulin, insulinotropin, heparin, calcitonin, octreotide, endorphin, TRH, NT-36 or N-[[(s)-4-oxo-2-azetidinyl]carbonyl]L-histidyl-L-prolinamide], liprecin, pituitary hormones (such as HGH, HMG, HCG, desmopressin acetate), follicile luteoids, a-ANF, growth factor releasing factor (GFRF), b-MSH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, eprostenol (platelet aggregation inhibitor), glucagon, hirulog, hyaluronidase, interferon, interleukin-2, menotropins (such as urofollitropin (FSH) and LH), oxytocin, streptokinase, tissue plasminogen activator, urokinase, vasopressin, desmopressin, ACTH analogs, ANP, ANP clearance inhibitors, angiotensin II antagonists, antidiuretic hormone agonists, antidiuretic hormone antagonists, bradykinin antagonists, CD4, ceredase, CSF's, enkephalins, FAB fragments, IgE peptide suppressors, IGF-1, neurotrophic factors, colony stimulating factors, parathyroid hormone and agonists, parathyroid hormone antagonists, prostaglandin antagonists, pentigetide, protein C, protein S, renin inhibitors, thymosin alpha-1 antitrypsin (recombinant), and TGF-beta.

Figure 4:
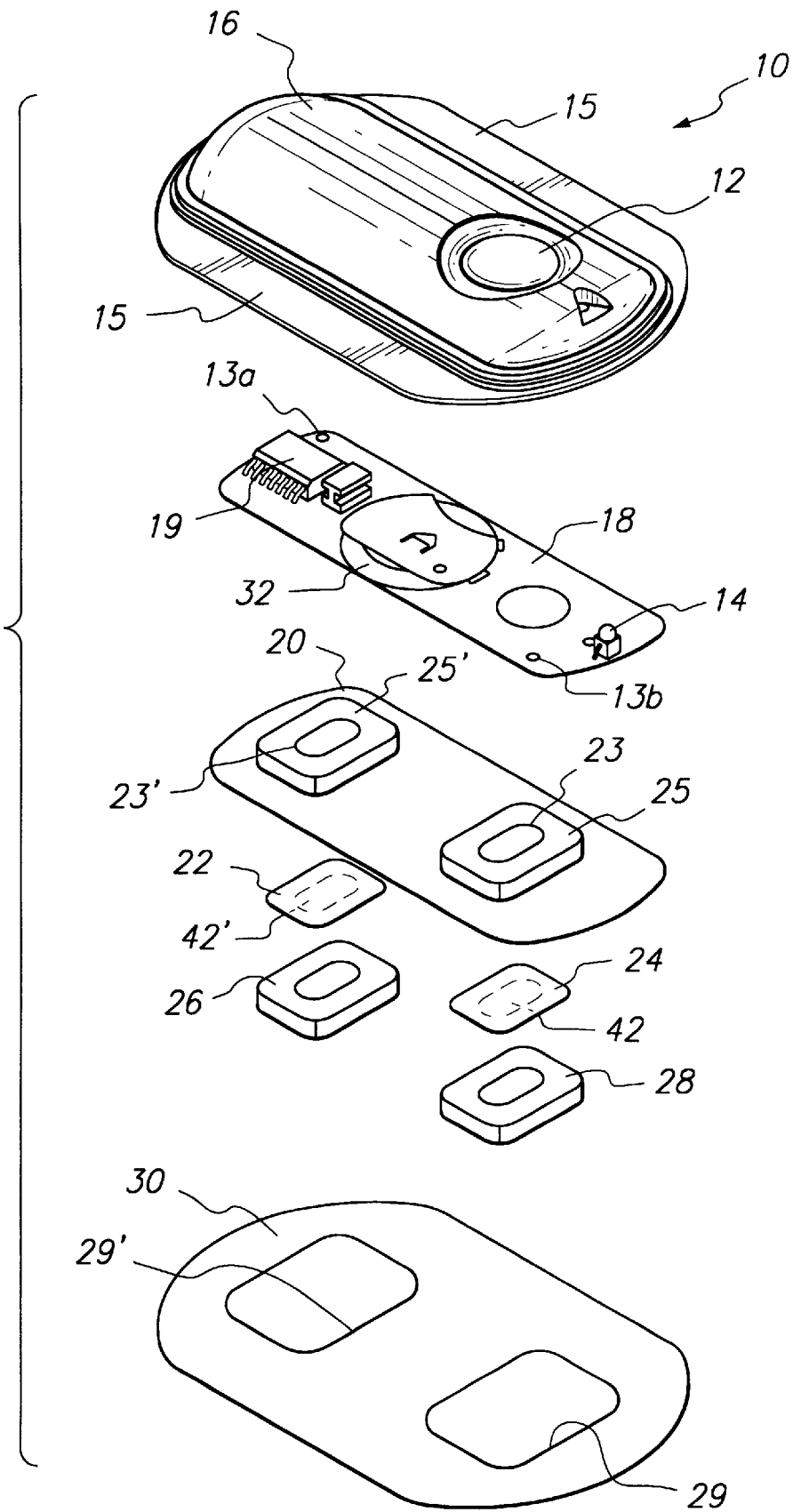
FIG. 4 is an exploded perspective view of an exemplary electrotransport device of the present invention.

FIG. 4 illustrates a representative electrotransport delivery device that may be used in conjunction with the present invention. Device 10 comprises an upper housing 16, a circuit board assembly 18, a lower housing 20, electrodes 42 and 42', electrolyte gel reservoirs 26 and 28, and skin-compatible adhesive 30. Upper housing 16 has lateral wings 15 which assist in holding device 10 on a patient's skin. Upper housing 16 is preferably composed of an injection moldable elastomer (e.g., ethylene vinyl acetate). Printed circuit board assembly 18 comprises one or more electrical components 19 (e.g., an integrated circuit) and battery 32. Circuit board assembly 18 is attached to housing 16 by posts (not shown in FIG. 4) passing through openings 13a and 13b, the ends of the posts being heated/melted in order to heat stake the circuit board assembly 18 to the housing 16. Lower housing 20 is attached to the upper housing 16 by means of adhesive 30, the skin distal side of adhesive 30 being adhered to both lower housing 20 and upper housing 16 including the bottom surfaces of wings 15.

The outputs (not shown in FIG. 4) of the circuit board assembly 18 make electrical contact with electrodes 42' and 42 through current collectors 22 and 24, respectively. Current collectors 22 and 24 are composed of an electrically conductive adhesive which adheres to the skin distal sides of electrodes 42' and 42, respectively. The skin distal sides of current collectors 22 and 24 adhere to the circuit outputs (not shown) on the underside of circuit board assembly 18 through openings 23', 23 formed in lower housing 20. Electrodes 42 and 42', in turn, are in direct mechanical and electrical contact with the skin-distal sides of electrolyte gel reservoirs 26 and 28. The skin-proximal sides of electrolyte gel reservoirs 26, 28 contact the patient's skin through the openings 29', 29 in adhesive 30.

Device 10 optionally has a feature which allows the patient to self-administer a dose of drug by electrotransport. Upon depression of push button switch 12, the electronic circuitry on circuit board assembly 18 delivers a predetermined DC current to the electrodes/electrolyte reservoirs 42', 42 and 26, 28 for a delivery interval of predetermined length. The push button switch 12 is conveniently located on the topside of device 10 and is easily actuated through clothing. A double press of the push button switch 12 within a short time period, e.g., three seconds, is preferably used to activate the device for delivery of drug, thereby minimizing the likelihood of inadvertent actuation of the device 10. Preferably, the device transmits to the user a visual and/or audible confirmation of the onset of the drug delivery interval by means of LED 14 becoming lit and/or an audible signal from, e.g., a "beeper". Drug is delivered through the patient's skin by electrotransport, e.g., on the arm, over the predetermined delivery interval.

In accordance with the present invention, the electrodes 42 and 42' sit in depressions in the skin distal sides of electrolyte gel reservoirs 28 and 26, respectively. Because the depth of these depressions are approximately equal to the thickness of electrodes 42 and 42', there exists an oval-shaped common boundary in each of the two electrode assemblies of the device 10. Thus, there is a common boundary between the current collector 22, the electrode 42' and the electrolyte gel reservoir 26. There is also a common boundary between the current collector 24, the electrode 42 and the electrolyte gel reservoir 28. Although the device 10 illustrates the common boundary on both "sides" (i.e., the anodic side and the cathodic side) of the device 10, it is within the scope of the present invention to use the common boundary condition on only one side (i.e., the anodic side or the cathodic side) of the electrotransport device 10.

The push button switch 12, the electronic circuitry on circuit board assembly 18 and the battery 32 are adhesively "sealed" between upper housing 16 and lower housing 20. Upper housing 16 is preferably composed of rubber or other elastomeric material. Lower housing 20 is preferably composed of a plastic or elastomeric sheet material (e.g., polyethylene or polyethylene terephthalate copolymer) which can be easily molded to form depressions 25, 25' and cut to form openings 23, 23'. The assembled device 10 is preferably water resistant (i.e., splash proof) and is most preferably waterproof. The system has a low profile that easily conforms to the body, thereby allowing freedom of movement at, and around, the wearing sit. The electrolyte gel reservoirs 26 and 28 are located on the skin-contacting side of the device 10 and are sufficiently separated to prevent accidental electrical shorting during normal handling and use.

The device 10 adheres to the patient's body surface (e.g., skin) by means of a peripheral (i.e., surrounding the periphery of electrolyte gel reservoirs 26 and 28) adhesive 30. The adhesive 30 has adhesive properties which assures that the device 10 remains in place on the body during normal user activity, and yet permits reasonable removal after the predetermined (e.g., 24-hour) wear period.

The electrolyte gel reservoirs 26 and 28 each comprise liquid electrolyte contained in a gel matrix. In the case where device 10 is a transdermal drug delivery device, at least one of the gel reservoirs 26 and 28 contains a drug solution or suspension. Drug concentrations in the range of approximately $1 \times 10^{-4}$ M to 1.0 M or more can be used, with drug concentrations in the lower portion of the range being preferred. Suitable polymers for the gel matrix may comprise essentially any nonionic synthetic and/or naturally occurring polymeric materials. A polar nature is preferred when the active agent is polar and/or capable of ionization, so as to enhance agent solubility. Optionally, the gel matrix will be water swellable. Examples of suitable synthetic polymers include, but are not limited to, poly(acrylamide), poly(2-hydroxyethyl acrylate), poly(2-dydroxypropyl acrylate), poly(N-vinyl-2-pyrrolidone), poly(n-methylol acrylamide), poly(diacetone acrylamide), poly(2-hydroxylethyl methacrylate), poly(vinyl alcohol) and poly (allyl alcohol). Hydroxyl functional condensation polymers (i.e., polyesters, polycarbonates, polyurethanes) are also examples of suitable polar synthetic polymers. Polar naturally occurring polymers (or derivatives thereof) suitable for use as the gel matrix are exemplified by cellulose ethers, methyl cellulose ethers, cellulose and hydroxylated cellulose, methyl cellulose and hydroxylated methyl cellulose, gums such as guar, locust, karaya, xanthan, gelatin, and derivatives thereof. Ionic polymers can also be used for the matrix provided that the available counterions are either drug ions or other ions that are oppositely charged relative to the active agent.

While the invention has been described in conjunction with the preferred specific embodiments thereof, it is to be understood that the foregoing description as well as the examples, which follow, are intended to illustrate and not limit the scope of the invention. Other aspects, advantages and modifications within the scope of the invention will be apparent to those skilled in the art.

Comparative Example 1

Figure 8:
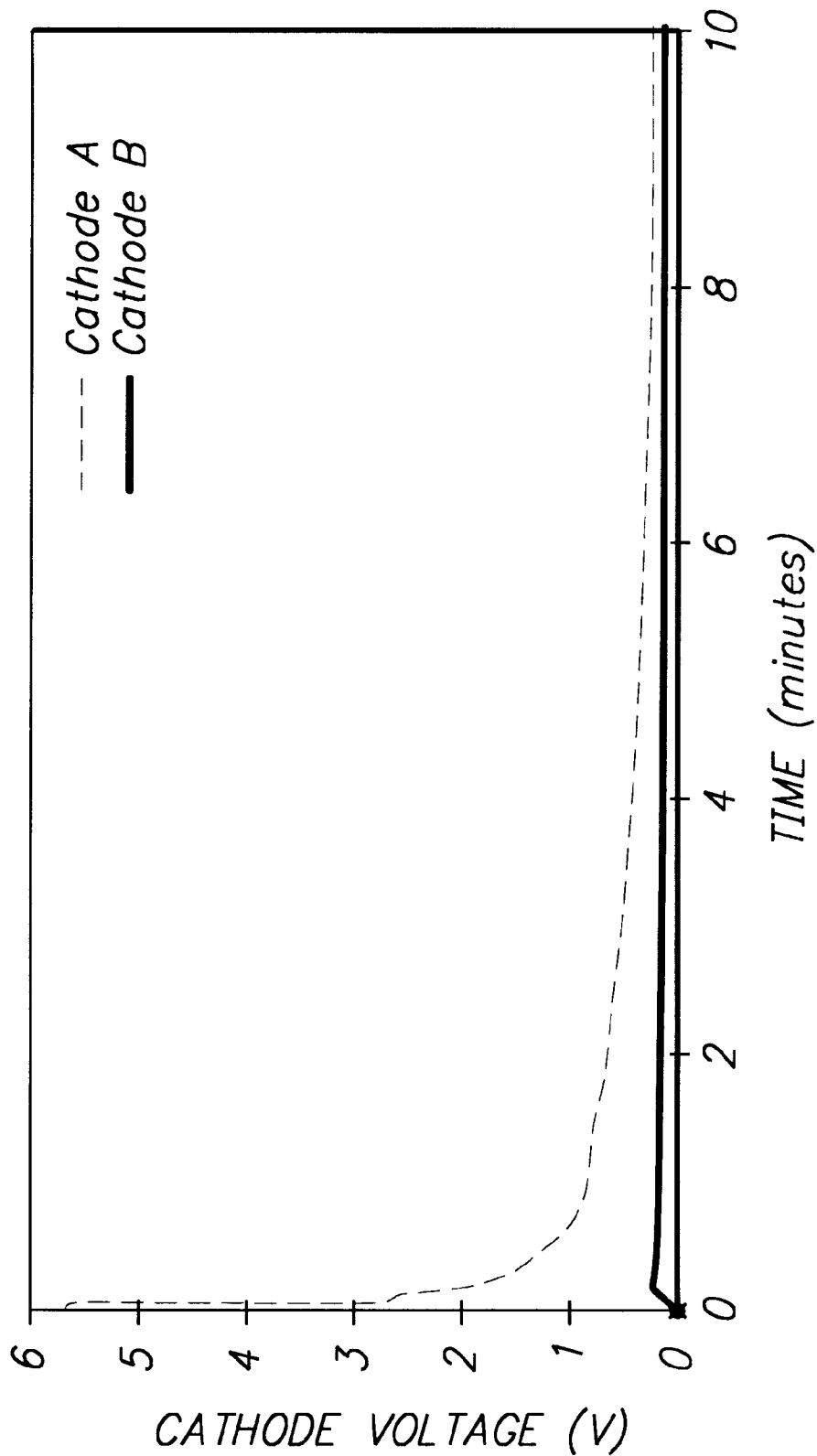

Shown in FIG. 8 is a comparison between (1) a prior art cathodic electrode assembly assembly according to FIG. 1 using a silver chloride cathode but no common boundary condition; and (2) a cathodic electrode assembly according to FIGS. 2 and 3 of the present invention, also using a silver chloride cathode and utilizing a common boundary between the current collector, the electrode and the liquid electrolyte.

The prior art cathodic electrode assembly (Cathode A) included a silver chloride foil cathode laminated to a current collector consisting of an electrically conductive adhesive having a sheet resistance of 10 ohm/square. The foil had an area of 2.85 cm$^2$, and the liquid electrolyte was a saline-containing gel. In Cathode A, the gel was placed in contact with the silver chloride foil but not in contact with the conductive adhesive. Thus, there was no common boundary in accordance with the present invention. The gel/foil contact area was 2.0 cm$^2$.

The cathodic electrode assembly of the present invention (Cathode B) included a silver chloride foil laminated to an electrically conductive adhesive, also having a sheet resistance of 10 ohm/square. The foil was a circular disk with an area of 1 cm$^2$, the adhesive had an area of 2.85 cm$^2$. Therefore, the gel/electrode contact area was 1.0 cm$^2$ and the length of the common boundary was equal to the perimeter of the electrode; 3.54 cm. The prior art cathode was a 0.05 mm (0.002 inch) thick AgCl strip. Cathode B had a smaller silver chloride foil (i.e., 1.0 cm$^2$) than cathode A.

The silver chloride foil was made from silver chloride strip supplied by Engelhard-CLAL of Carteret, N.J. The silver chloride strip had a thickness of 0.051 mm (0.002 inch) and was cut and laminated to the pieces of electrically conductive adhesive.

In the cell assemblies for both cathodic electrode examples, the liquid electrolyte/gel formulation was about 10 ml of 15% polyvinyl alcohol (PVOH), 2% hydroxy propyl methyl cellulose (HPMC), 0.1 M NaCl, and the remainder deionized water. The initial pH of the saline was 6.26.

Both electrode assemblies were discharged under identical current densities of 0.3 mA/cm$^2$ (because Cathode A had a larger surface area (2 cm$^2$) than Cathode B (1 cm$^2$), the discharge current for Cathode A (0.6 mA) was correspondingly higher than the discharge current for Cathode B (0.3 mA)). The discharge was conducted by electrically connecting the cathodic electrode assembly to the negative pole of a galvanostat. A silver foil anode was electrically connected to the positive pole of the galvanostat and placed against the free surface of the gel. During discharge, the voltages of cathodes A and B were measured versus Ag/AgCl quasi-reference electrodes.

As illustrated in FIG. 8, the discharge behavior of the cathodes were significantly different during the early period of discharge (i.e. the lag-time period). As shown in FIG. 8, The prior art cathode (Cathode A) had an initial discharge voltage (i.e., start-up voltage) of 5.68 V, whereas the cathode of the present invention (Cathode B) had a start-up voltage of only 0.21 V. The lag time was defined in these experiments as the time required for the voltage applied by the galvanostat to fall below 0.30 V. The lag time for Cathode A was 7.1 minutes, whereas the lag time for Cathode B was only 9 seconds.

Additional experiments were run on three prior art cathodes and three cathodes of the present invention as described immediately above. The average start-up voltages for the prior art cathodes was 3.71 volts while the average start-up voltages for the three cathodes of the present invention was 0.41 volts. The average lag time for the prior art cathodes was 9.8 minutes while the average lag times for the three cathodes of the present invention was only 8.6 seconds.

In an electrotransport system or almost any medical device, it is highly preferrable to have a low start-up voltage and lag time resulting in improved performance and reduced electrical power consumption. In sum, the performance of the present invention was unexpectedly superior to the prior art cathodes.

Comparative Example 2

Two electrotransport devices (device A and device B) are constructed, each of the devices having a power source and a pair of electrode assemblies, one anodic and the other cathodic. Each of the electrode assemblies includes a copper foil current collector, an electrode and a polyvinyl alcohol gel reservoir containing saline. The cathodic electrode assembly in each of the devices comprises a silver chloride cathode and has the configuration shown in FIG. 1, i.e., there is no common boundary condition in the cathodic electrode assembly of either device. The anodic electrode assembly of device A is comprised of a leuco-polyaniline strip and has the configuration shown in FIG. 1, i.e., there is no common boundary condition in the anodic electrode assembly of device A. On the other hand, the anodic electrode assembly of device B is comprised of a leuco-polyaniline strip and has the configuration shown in FIG. 2, i.e., there is a common boundary condition in the anodic electrode assembly of device B. The electrode assemblies of each of the devices are connected to a galvanostat which applies an electrotransport current of 0.5 mA. The start-up voltage of device B having the common boundary condition leuco-polyaniline anode is significantly lower than the start-up voltage of device A having the leuco-polyaniline anodic electrode assembly with no common boundary condition. Furthermore, the lag time for the galvanostat power source to reach an output voltage of 0.3 volts is significantly shorter with device B compared to device A.

Having thus generally described our invention and described in detail certain preferred embodiments, it will be readily apparent that various modifications to the invention may be made by persons skilled in this art without departing from the scope of this invention and which is limited only by the following claims.

What is claimed is:

1. An electrotransport device for delivering or sampling an agent through a body surface, the device including an anodic electrode assembly, a cathodic electrode assembly and a source of electrical power electrically connected to the anodic and cathodic electrode assemblies, at least one of the anodic and cathodic electrode assemblies comprising:

an electrode composed at least in part of a solid phase electrochemically reactive material, the electrode having an initial electrical resistance, the electrode becoming less resistant upon exposure to electric current;

an electrolyte reservoir containing therein the agent to be delivered or capable of receiving the agent to be sampled, said reservoir when in use positioned in ion-transmitting relation with the body surface;

an electric current collector, discrete from the electrode, having an electrical resistance less than the electrical resistance of the electrode, the current collector conducting electric current between the power source and the electrode;

wherein at a time when the device begins applying electrotransport current, the electrode, the current collector and the electrolyte reservoir form a common boundary.

2. The device of claim 1, wherein the electrode assembly having the common boundary condition is the cathodic electrode assembly and the electrochemically reactive material is reducible.

3. The device of claim 2, wherein the reducible material is selected from the group consisting of metal compounds, metal complexes, intercalation compounds, carbon intercalation hosts hosting an alkali metal, and electrochemically reducible polymers.

4. The device of claim 3, wherein the reducible material is a compound or a complex having a formula MX, wherein M is an electrochemically reducible metal and X is selected from the group consisting of halides, polymeric anions, and low molecular weight anions.

5. The device of claim 4, wherein M is selected from the group consisting of silver, copper and zinc.

6. The device of claim 4, wherein MX comprises a silver halide.

7. The device of claim 3, wherein the intercalation compound has a formula $M_x(WO_3)_y$, wherein M is a metal, x is a number greater than or equal to zero, and y is a number greater than zero.

8. The device of claim 3, wherein the metal compound has a formula $M_x[Fe(CN)_6]_y$, wherein x and y are numbers greater than zero.

9. The device of claim 2, wherein the electrode comprises a silver chloride foil.

10. The device of claim 1, wherein the agent is a body analyte to be transdermally sampled by the device, the device having a body analyte-receiving reservoir in at least one of the anodic and cathodic electrode assemblies.

11. The device of claim 10, wherein the body analyte is non-ionic and is received in at least one of (i) a cathodic reservoir in the cathodic electrode assembly and (ii) an anodic reservoir in the anodic electrode assembly.

12. The device of claim 11, wherein the non-ionic body analyte is glucose.

13. The device of claim 10, wherein the body analyte is cationic and is received in a cathodic reservoir in the cathodic electrode assembly.

14. The device of claim 10, wherein the body analyte is anionic and is received in an anodic reservoir in the anodic electrode assembly.

15. The device of claim 1, wherein the electrode has an initial electrical sheet resistance of greater than 100 ohms/square.

16. The device of claim 15, wherein the current collector has an electrical sheet resistance that is less than one-half the sheet resistance of the electrode.

17. The device of claim 1, wherein the electrode comprises a polymer matrix and the electrochemically reactive material is contained in said matrix.

18. The device of claim 17, wherein the polymer matrix, at the time when the device begins applying electrotransport current, is substantially free of any electrically conductive material.

19. The device of claim 1, wherein the electrode assembly having the common boundary condition is the anodic electrode assembly and the electrochemically reactive material is oxidizable.

20. The device of claim 19, wherein the oxidizable material is selected from the group consisting of a leuco form of polyaniline and transition metal halide-intercalated carbon or graphite.

21. The device of claim 19, wherein the anodic electrode comprises a polyaniline sheet.

22. The device of claim 1, wherein the agent is a therapeutic agent to be delivered by the device through skin, at least one of the anodic and cathodic electrode assemblies having a reservoir containing the therapeutic agent.

23. The device of claim 22, wherein the agent is cationic and is contained in an anodic reservoir within the anodic electrode assembly, the anodic electrode assembly being a donor electrode assembly.

24. The device of claim 22, wherein the agent is anionic and is contained in a cathodic reservoir within the cathodic electrode assembly, the cathodic electrode being a donor electrode.

25. The device of claim 1, wherein the electrode is oxidized or reduced upon exposure to electric current to a form having a lower electrical sheet resistance than said initial electrical sheet resistance.

26. The device of claim 1, wherein the power source applies an electric current i through the current collector to the electrode, the common boundary having a length I, the ratio of I:i being at least 0.1 cm/mA.

27. The device of claim 1, wherein the common boundary has a length of at least 0.1 cm.

28. The device of claim 1, wherein the solid electrochemically reactive material has a solubility in the electrolyte of less than about 1 mg/ml.

29. The device of claim 1, wherein the common boundary has a shape selected from the group consisting of linear, rectangular, circular, and elliptical.

30. The device of claim 1, wherein the electrode assembly with the common boundary has a plurality of said common boundaries.

31. The device of claim 1, wherein the electrode consists essentially of the electrochemically reactive material.

32. The device of claim 1, wherein the current collector is comprised of a material selected from the group consisting of metals and carbon.

33. The device of claim 1, wherein the current collector is selected from the group consisting of an electrically conductive adhesive and an electrically conductive trace.

34. The device of claim 1, wherein the electrolyte reservoir comprises an aqueous solution.

35. The device of claim 1, wherein the electrolyte reservoir comprises a gel.

36. The device of claim 1 wherein the electrode has an initial electrical sheet resistance of greater than about 10,000 ohms/square.

37. The device of claim 1 wherein the electric current collector has an initial electrical sheet resistance of less than about 50,000 ohms/square.

38. The device of claim 1 wherein the electric current collector has an initial electrical sheet resistance of less than about 1,000 ohms/square.

39. The device of claim 1 wherein the electric current collector has an initial electrical sheet resistance of less than about 10 ohms/square.

* * * * *